(12) United States Patent
Baas et al.

(10) Patent No.: US 6,879,168 B2
(45) Date of Patent: Apr. 12, 2005

(54) ICE DETECTION SYSTEM

(75) Inventors: Jack Baas, Thousand Oaks, CA (US); Clayton Larson, Acton, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 10/117,271

(22) Filed: Apr. 8, 2002

(65) Prior Publication Data

US 2003/0189434 A1 Oct. 9, 2003

(51) Int. Cl.$^7$ .................................................. G01R 27/26
(52) U.S. Cl. ......................... 324/671; 324/662; 324/664
(58) Field of Search .................................. 340/560, 962; 73/170.26; 324/71.1, 671, 699, 663, 661, 664, 691; 333/17.3, 32, 253, 263, 34; 438/17

(56) References Cited

U.S. PATENT DOCUMENTS

| | | | |
|---|---|---|---|
| 4,766,369 A | 8/1988 | Weinstein | .................... 324/670 |
| 5,569,850 A | 10/1996 | Rauckhorst, III | ......... 73/170.26 |
| 5,874,672 A | 2/1999 | Gerardi et al. | ........... 73/170.26 |
| 6,052,056 A | 4/2000 | Burns | .......................... 340/853 |
| 6,384,611 B1 * | 5/2002 | Wallace et al. | .............. 324/671 |

\* cited by examiner

*Primary Examiner*—Vincent Q. Nguyen
(74) *Attorney, Agent, or Firm*—Koestner Bertani LLP

(57) ABSTRACT

The invention is a system for determining the presence of ice on the surface of a structure. The system includes a guard layer mounted to the surface. A non-conductive layer is mounted on top of the ground plane. First and second electrodes made of a resistive material mounted on the non-conductive layer. First and second electrical leads having first ends of attached to first and second electrodes, respectively. The first and second leads having impedance equal to the impedance of the first ends thereof with the impedance of the first and second leads decreasing toward the second ends thereof.

25 Claims, 2 Drawing Sheets

ICE DETECTION SYSTEM

BACKGROUND OF THE INVENTION

1. Field of the Invention

The invention relates to the field of ice detection systems for aircraft and, in particular, to an ice detection system for low observable aircraft.

2. Description of Related Art

Aircraft icing can occur under certain atmospheric conditions. The icing primarily forms on the leading edge of the wings. Such ice accretion, if allowed to build up, can cause a loss of lift, which can, in extreme cases, cause the aircraft to crash. Thus modern commercial aircraft incorporated anti-icing devices. For example, large aircraft incorporate hot air ducts along the leading edges of wings. Hot bleed air from the compressor stages of the turbine engines are fed through these ducts, melting the ice. Smaller aircraft use inflatable boots that can be pulsed to expand and contract, breaking up the ice. Other systems involve the use of electromechanical actuators that flex the outer skin of the wings breaking up the ice. On most small aircraft, de-icing systems are not employed. Therefore, the pilot is required to fly the aircraft out of the "ice forming" environment. All aircraft having de-icing systems must have ice formation sensors strategically placed to sense the ice forming so that the de-icing system can be actuated in a timely manner.

Even on aircraft that do not have de-icing systems, detection systems are often incorporated. The most obvious method is visual examination by the flight crew. While the pilot can usually see the wings on small general aviation aircraft, on larger aircraft the wings are not always visible from the flight station. At night, visual examination may not be possible. Thus an ice detection system will give the pilot warning and allow him or her to fly the aircraft out of the area. If the aircraft is unmanned, the remote operator will have the same capability.

There are numerous types of ice detection systems available, for example, U.S. Pat. No. 6,052,056 "Substance Detection System" by J. D. Burns, et al. In this system a modulated light source is directed to an optical sensor located in an area where ice will tend to accumulate, such as an aerodynamic surface or engine inlet. The sensor transmits light back to a detector that is proportional to the amount of ice on the surface.

Another approach is to use ultrasonic transducer guided waves, which are applied to the aircraft's skin. The waves interact with the reflective geometry of the skin and a portion of the waves scatter back to the transducer. By monitoring the amplitude, frequency change, etc. of the returned waves, ice build up on the skin can be identified. Magnetostrictive ice detection is also available. Sensors vibrate ultrasonically at a set frequency. As ice accretes on a probe, the vibrational frequency decreases, which is detected signaling the to remove the ice. In another system a detector operates periodically by heating a temperature element to a constant temperature. A microprocessor measures the element's rate of temperature increase by comparing the time it takes the element to pass through two reference temperatures. Since the melting process absorbs considerable energy, the temperature increases at a slower rate when ice has accumulated.

Another approach is to use capacitance probes mounted on the external surface. Examples of these can be found in U.S. Pat. No. : 4,766,369 "Ice Detector System" by L. M. Weinstein; U.S. Pat. No. 45,569,850 "Ice Detector" by R. L. Raunchorst, 111; and 5,854,672 "Apparatus And Method For Determining The Existence Of Ice Or Water On a Surface From The Capacitance Between Electrodes On Said Surface" by J. J. Gerardi, et al. In these devices, capacitance probes, generally spaced conductive electrodes encapsulated in a non-conductive substrate, are mounted on a surface where ice will tend to accumulate. The accumulating ice, of course, will change the capacitance of the probe, which can be sensed, by a capacitance measuring circuit.

The problem with existing capacitance probe type ice detection systems is that they do not lend themselves to use on low radar observable aircraft. The lead wires to the probes and the probes themselves tend to increase the radar signature on the aircraft. The conductive probes and lead wires scatter the incoming radar signals and have radar cross-sections that are much to large for low observable aircraft applications.

Thus, it is a primary object of the subject invention to provide an ice detection system for an aircraft.

It is a still further object of the subject invention to provide an ice detection system for an aircraft having a low radar cross-section.

An additional object of the subject invention is to provide an ice detection system using capacitance probes for an aircraft having a low radar cross-section.

SUMMARY OF THE INVENTION

The invention is a system for determining the presence of ice on an external surface subject to ice accretion thereon of an aircraft designed with a low radar cross-section. For example, the leading edges of the wings, tails, or engine inlets are the most likely areas where ice detection systems are required. For example, the leading edge of a wing, tail, or engine inlet of a low radar cross-section aircraft typically includes a non-metallic outer skin made of a dielectric material that is filled with a structural bulk absorber. The bulk absorber is typically either a "loaded" foam or coated honeycomb core. Thus the system for determining the presence of ice on an external surface of a structure includes a guard layer, made of a layer of resistive material, for mounting on the external surface. A non-conductive layer is mounted on top of the guard layer. First and second electrodes made of a resistive material are mounted on the non-conductive layer. Preferably, the electrodes are parallel to each other. Preferably, the resistive material of the first and second electrodes has a nominal resistance of 400 ohms per linear inch of length.

The system further includes first and second electrical leads having first and second ends, with the first ends of the leads attached to the first and second electrodes, respectively. The leads extend parallel to each other in opposite directions from each other. The first ends of first and second leads have an impedance equal to the impedance of the first and second electrodes with the resistance decreasing toward the second ends thereof to around a nominal value of 50 ohms per square. The non-conductive layer and guard layer extend under the entire length of the first and second leads. Preferably, the resistance of the guard layer tapers from a nominal value of 750 ohms per square under the electrodes to around 50 ohms per square at the second ends of the leads.

Preferably, a layer of semi-conductive material is bonded over the first and second electrodes and a coating of dielectric material covers the non-conductive layer surrounding the first and second electrodes and the layer of semi-conductive material and extends to the second ends of the first and second leads.

Thus the non-conductive layer, guard layer, the first and second electrodes with the semi-conductive coating there over, first and second leads, and the coating of dielectric material form an assembly. To insure a smooth external surface, the external surface includes a recess and the assembly is mounted in the recess by an adhesive. Additional dielectric material fills any remaining portions of the recess. The second ends of the leads are electrically connected to a control module, which measures any capacitance change in the electrodes and sends a signal to the pilot of the aircraft.

In a preferred version an adhesive layer is applied to the guard layer and over which is mounted a strippable cover. Thus, the system is self-contained and can be stored with ease until installation is required. To install, one need only peel the cover off and insert the system into the recess on the airfoil leading edge. Of course, the system must be sized for the particular surface and the design values of the resistive sheet, electrode and strips will also vary from application to application.

The novel features which are believed to be characteristic of the invention, both as to its organization and method of operation, together with further objects and advantages thereof, will be better understood from the following description in connection with the accompanying drawings in which the presently preferred embodiment of the invention is illustrated by way of example. It is to be expressly understood, however, that the drawings are for purposes of illustration and description only and are not intended as a definition of the limits of the invention.

DESCRIPTION OF PREFERRED EMBODIMENT

Figure 1:
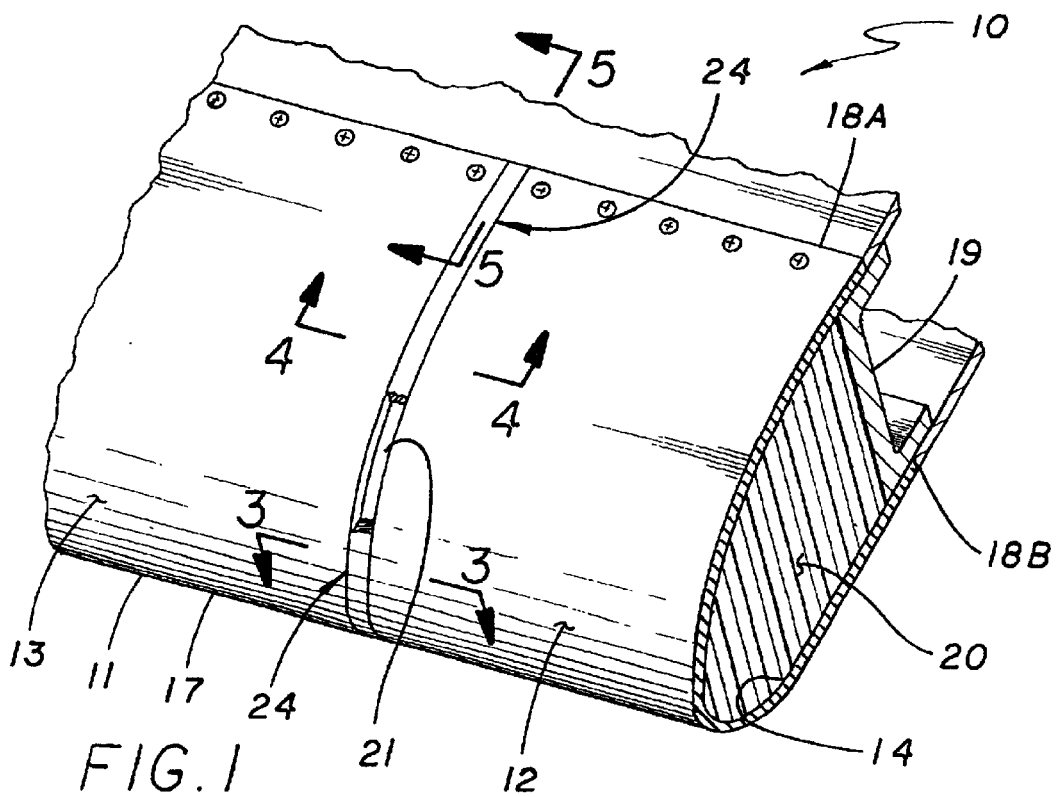
FIG. 1 is a partial perspective view of the leading edge portion of the wing of an aircraft having a low radar cross-section.
Figure 3:
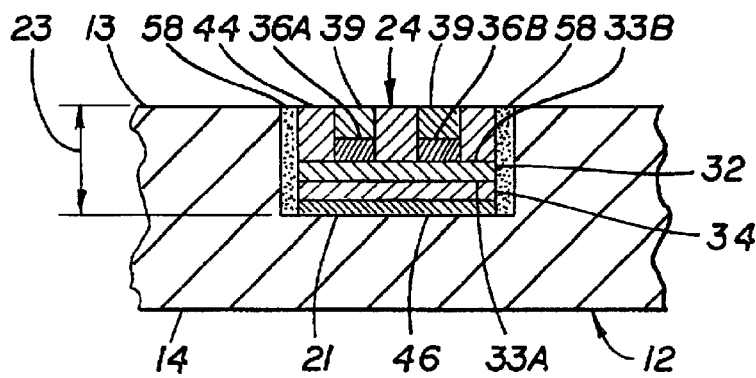
FIG. 3 is a partial cross-sectional view of FIG. 1 taken along the line 3—3.

In FIGS. 1 and 3, an illustration of a leading edge portion of a wing 10 of an aircraft designed to have a low radar cross-sectional area is shown. The leading edge portion 11 includes an outer skin 12 made of a dielectric material having an external surface 13, an internal surface 14, a leading edge 17, and the aft ends 18A and 18b, which are joined to a bulkhead 19. The skin 12 is typically a composite material such as Kevlar® filaments in a resin matrix, manufactured by the manufactured by the E.I. DuPont de Nemours & Company, Delaware. The loading edge portion 11 is filled with a bulk absorber 20, which can be a loaded foam core or coated honeycomb core bonded to the skin 12. The foam or honeycomb core would also be made of a dielectric material. A small recess 21 is located on surface 14 and extends from the end 18A, across the leading edge 37 and to end 18B. The recess 21 has width indicated by numeral 22 of approximately two inches and a depth, indicated by numeral 23, or approximately 0.030 inch. However, it must be noted that actual required dimensions will vary from application to application.

Figure 2:
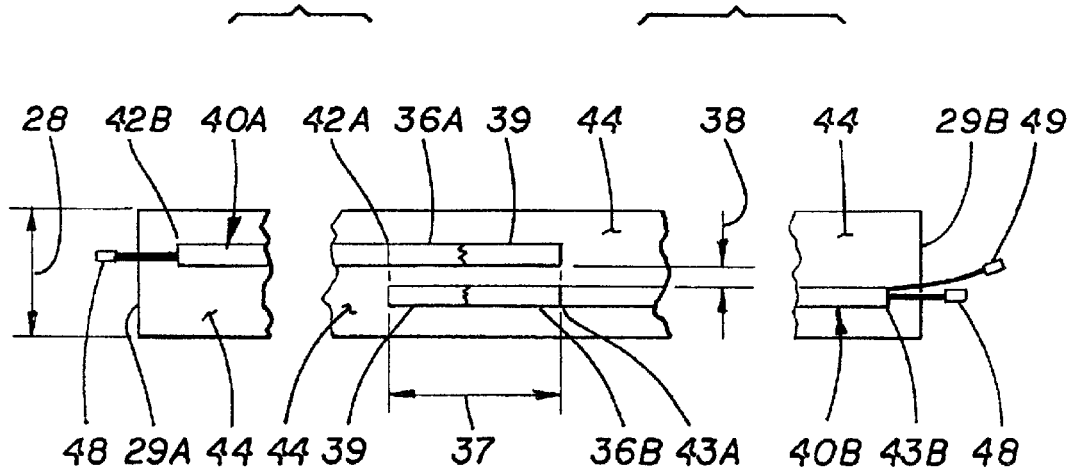
FIG. 2 is a partial view of the system prior to installation in to the wing of the aircraft.
Figure 4:
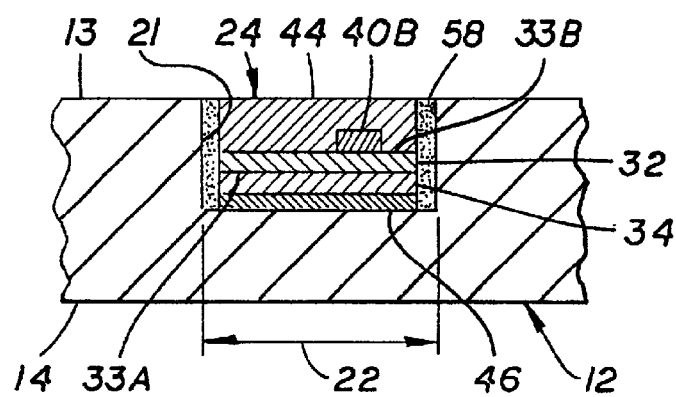
FIG. 4 is a partial cross-sectional view of FIG. 1 taken along the line 4—4 shown in FIG. 1.

Still referring to FIGS. 1 and 3, and additionally to FIGS. 2 and 4, the detector system, indicated by numeral 24 has a length 26 that is a little less than the overall length of the recess 21. The width 28 of the detector assembly 24 is a little less than the width 22 of the recess 21. The detector system 24, includes a non-conductive substrate or layer 32, typically, a polycarbonate sheet, having first and second sides 33A and 33B extending along the entire length 26. A guard layer 34 made of a resistive material, such as a graphite or carbon impregnated urethane ink, is silk screened on side 33A of the layer 32 along the entire length. The resistive value of the guard layer 34 will be subsequently discussed. A pair of resistive wire electrodes 36A and 36B, which act as the capacitance probe, made of a resistive material such as graphite or carbon impregnated urethane ink, are silk-screened on the opposite side 33B of the layer 32. The electrodes should have a nominal resistance of 400 ohms per linear inch of length with an overall length, indicated by numeral 37, of a bout two inches. The electrodes 36A and 36B should be separated by a distance, indicated by numeral 38, of about 0.1 inch. A semi-conductive urethane cover 39 is placed over the electrodes 36A and 36B to provide protection, but only over the two-inch length 37.

The electrodes 36A and 36B are connected to electrical leads in the form of resistive strips 40A and 40B, respectively. The strips 40A and 40B can also comprise loaded urethane ink silk screened onto side 33B of the layer 32. At the ends 42A and 43A of the strips 40A and 40B, respectively, the resistance of the strips should be equal to the electrodes 36A and 36B. Thereafter, the resistance should decrease such that it approaches a nominal value of 50 ohms per square at ends 42B and 43B. This could be accomplished by silk-screening the strips 40A and 40B in steps using higher "loaded" ink as ends 42A and 43B are approached. The resistive value of the guard layer 34 should be a nominal 750 ohms per square under the electrodes 36A and 36B and taper in value to a nominal 50 ohms per square at the second ends 42B and 43B of the strips 40A and 40B, respectively. The guard layer 34 isolates the electrodes 36A and 36B from spurious electrical signals (noise) generated with the aircraft. Thereafter, the entire side 33B of the layer 32 is covered with a non-conductive coating 44, for example urethane sealant or the like, such that the entire surface 32 is covered to a level equal to the semi-conductive urethane cover 39. Thus the strips 40A and 40B are also protected from rain erosion and the like. The completed system 24 is bonded in the recess 21 by an adhesive coating 46 applied to the resistive layer 34 on the surface 33A of the layer 32.

Figure 5:
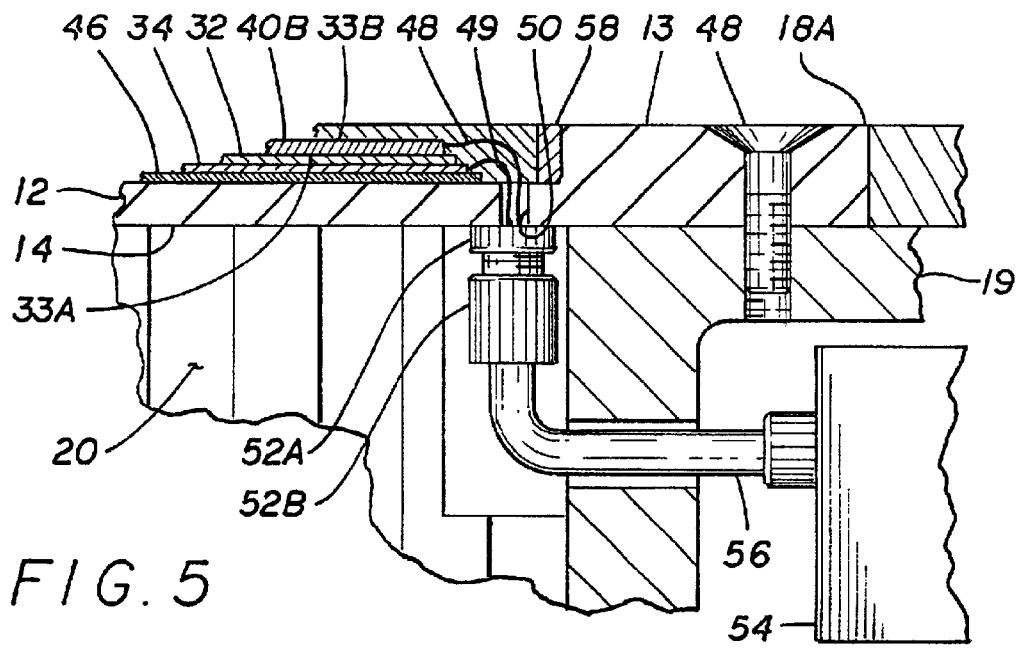
FIG. 5 is a partial cross-sectional view of FIG. 1 taken along the line 5—5 shown in FIG. 1.

Referring to FIG. 5, the end 20A of the skin 14 is joined to the bulkhead 19 by fasteners 48. The end 43B of the strip 40B is joined to a wire 48, that extends through a hole 50 in the skin 12 and is connected to a coax connector half 52A joined to the internal surface 17 of the skin. The guard layer 34 in connected to ground by wire 49 that also extends through the hole 50 and connects to the exterior to the coax connector half 52A. An electronic module 54 that is used to sense capacitance changes in the electrodes 36A and 36B is connected via coax cable 56 and second connector half 52B to connector half 52A. While not illustrated, strip 40A is connected to the module 54 in a similar manner. Referring to FIGS. 3–5, the final step is to fill any gaps between the system 24 and recess 21 walls with a dielectric filler 58 such as urethane to eliminate any gaps.

Figure 6:
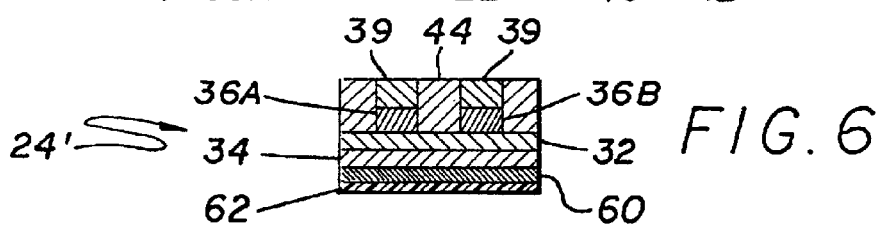
FIG. 6 is a cross-sectional view of an alternate design of the system.

In FIG. 6, an alternate design for the system, designated by numeral 31' is illustrated. Here all features are identical except that a layer of pressure sensitive adhesive 60 is applied directly to the resistive layer 34 and a strippable cover 62 applied there over. The advantage with this design is that the system 24' can be stored until ready for installation. The cover 62 can then be removed and, the system 24' installed in the recess 21, eliminating the need to apply an adhesive to the recess.

Again referring to FIGS. 2–5, manufacturing of the system can be easily accomplished by first silk-screening a coating a first side 33A of thin flexible polycarbonate sheet 32 with the resistive coating 34. Thereafter, electrodes 36A and 36B and strips 40A and 40B are silk screened on the second side 33B. Inert plugs (not shown) having the size and shape of the semi-conductive coatings 38 are placed over the electrodes. The wires 48 are attached to the ends 42B and 43B of the strips 40A and 40B. The second side 33B of the sheet is then coated with the non-conductive urethane cover 44. The inert plugs are removed and the holes filled with the semi-conductive urethane covers 39. Again referring to FIG. 6, If so desired, the adhesive coating 60 and removable cover 62 can be easily added.

In review, a capacitive ice detector senses the presence of an ice coating through an increase in measured capacitance. A coating of ice increases the dielectric constant in the region near the electrodes and raises the capacitance thereof. To have high sensitivity to ice formation the ice detector needs to be on the outer surface of the aircraft, adjacent to the ice coating. If the icing detector has direct current coupling with the ice, the resistance of the ice can be measured. The semi-conductive urethane cover 38 performs this function. High moisture content ice or wet ice has a low resistance compared to a low moisture content ice or dry ice. Hence, wet and dry ice can be discriminated through resistance measurement.

To have high measurement sensitivity to ice formation, the strips 40A and 40B that connect the electronic module 54 to electrodes 36A and 36B must have a capacitance that is much smaller than the capacitance of the electrodes. The capacitance of electrodes 36A and 36B have a nominal value of 1 picofarad. The capacitance of the strips 40A and 40B needs to be, at a minimum, a factor of 4, and preferably a factor of 10, less than the capacitance of electrodes or less than 0.25 picofarad. The capacitance of the strips 40A and 40B is reduced by physical separation and through the use of electrostatic shields. The conventional non-low observable method of electrostatic shielding is accomplished with the use of coaxial cables. The coaxial cable outer conductor provides the electrostatic shielding. However, the coaxial cable outer conductors will have a radar cross section that is much too large for low observable applications. The subject invention uses the guard layer, 34, for the electrostatic shield to reduce the capacitance between the feed lines, 40A and 40B. The guard layer is a tapered resistive film. The resistance values and taper function depends upon the electrical properties of the materials in the edge absorber design. The guard layer resistive values will be developed so the guard layer is an integral part of the edge absorber design. This will minimize the radar cross section of the guard layer.

In review, the capacitance and resistance measurement electronics use an alternating current signal with a nominal frequency of 10 kHz. With no ice on the capacitance probe, the measured impedance is in excess of 10 megohms. When ice coats the capacitance probe, the impedance is reduced up to a factor of five. The series resistance of the strips 40A and 40B and the resistive loss of guard layer 34 is much smaller than the measured impedance of the capacitance probe. Hence, the strips 40A and 40B and the guard layer 34 will not degrade the operation of the measurement electronics. Since the measurement impedance of the ice free capacitance probe is very high, the resistance between the strips 40A and 40B, the capacitance probe electrodes 36A and 36B need to be greater than a factor of three larger than the measured impedance. Therefore, the materials that surround the strips 40A and 40B and the electrodes 36A and 36B need to be a very high resistivity insulator.

In conclusion, it has been demonstrated that the above system can be manufactured and easily installed on an aircraft surface subject to icing. It has particular application to use on low observable aircraft that require a reduced radar cross-section where conventional capacitance measuring systems would produce an unacceptable radar signature due to the scattering of incoming radar signals caused by the conductive probes and lead wires. The electrodes 36A and 36B and strips 40A and 40B have a combined resistance on the order of a few thousand ohms. Actual effects of ice are on the order of a million ohms. Thus measurement of ice accumulation is readily made.

While the invention has been described with reference to particular embodiment, it should be understood that the embodiments is merely illustrative as there are numerous variations and modifications, which may be made by those skilled in the art. Thus, the invention is to be construed as being limited only by the spirit and scope of the appended claims.

INDUSTRIAL APPLICATION

The invention has application in the aircraft industry and, in particular, to a company making ice detection systems for aircraft.

What is claimed is:

1. A system for determining the presence of ice on an external surface of a structure, comprising:
    a guard layer;
    a non-conductive layer mounted on top of said guard layer;
    first and second electrodes made of resistive material mounted on said non-conductive layer; and
    first and second electrical leads having first and second ends, said first ends of said leads attached to first and second electrodes, respectively, said first and second leads having an impedance equal to the impedance of said first and second electrodes, with said impedance of said first and second leads decreasing toward said second ends thereof.

2. The system as set forth in claim 1 further comprising said first and second electrodes are parallel to each other in a spaced relationship.

3. The system as set forth in claim 2 wherein said resistive material of said pair of electrodes has impedance of 400 ohms per linear inch of length.

4. The system as set forth in claim 3 further comprising the resistivity of said guard layer decreasing from the area under said first and second electrodes toward the area under said second ends of said first and second leads.

5. The system as set forth in claim 4 further comprising the resistivity of said guard layer in said area under said first and second electrodes is 750 ohms per square and under said area under said second ends of said first and second leads is 50 ohms per square.

6. The system as set forth in claim 5 further comprising the resistivity of first and second leads decreasing from said first ends to a value of 50 ohms per square at said second ends.

7. The system as set forth in claim 6 further comprising a layer of semi-conductive material mounted over said first and second electrodes.

8. The system as set forth in claim 7 further including a coating of dielectric material covering said non-conductive layer surrounding said first and second electrodes and said semi-conductive material.

9. The system as forth in claim 8 wherein said external surface includes a recess and said non-conductive layer, said guard layer; and said first and second electrodes are mountable in the recess, and said coating of dielectric material also fills the remaining portion of the recess.

10. The system as set forth in claim 9 further comprising said first and second leads extend parallel to each other in opposite directions to each other.

11. The system as set forth in claim 10 wherein the spacing of said electrodes is 0.10 inch.

12. A system for determining the presence of ice on an external surface of a structure, the device comprising:
   a guard layer mountable to the surface;
   a non-conductive layer mounted on top of said guard layer;
   first and second electrodes made of resistive material mounted on said non-conductive layer in a parallel spaced relationship; and
   first and second electrical leads having first and second ends, said first ends of said first and second leads attached to first and second electrodes, respectively, said first and second leads having said first ends thereof with an impedance equal to the impedance of said first and second electrodes with the impedance of said first and second leads decreasing toward said second ends thereof.

13. The system as set forth in claim 12 wherein said first and second leads separate from each other such that said second ends of said leads are substantially further apart than said first ends.

14. The system as set forth in claim 13, further comprising said first and second leads extend parallel to each other in opposite directions to each other.

15. The system as set forth in claim 14, further comprising the resistivity of said guard layer decreasing from the area under said first and second electrodes toward the area under said second ends of said first and second leads.

16. The system as set forth in claim 15, further comprising a layer of semi-conductive material mounted over said first and second electrodes.

17. The system as set forth in claim 16, further including a coating of dielectric material covering said non-conductive layer surrounding said first and second electrodes and said semi-conductive material.

18. The system as set forth in claim 17 wherein said external surface includes a recess and said non-conductive layer, said guard layer; and said first and second electrodes are mounted in the recess, and said coating of dielectric material also fills the remaining portion of the recess.

19. The system as set forth in claim 15, or 16, or 17, or 18 wherein:
   the resistive material of said pair of electrodes has impedance of 400 ohms per linear inch of length;
   the resistivity of said guard layer in said area under said first and second electrodes is 750 ohms per square and under said area under said second ends of said first and second leads is 50 ohms per square; and
   the resistivity of said first and second leads decreasing from said first ends to a value of 50 ohms per square at said second ends.

20. A structure including an ice detection system, comprising:
   a guard layer;
   a non-conductive layer mounted adjacent said guard layer;
   first and second electrodes adjacent said non-conductive layer; and
   first and second electrical leads coupled to respective said first and second electrodes, wherein the resistivity of said guard layer tapers from one end of said first and second electrical leads to another end of said first and second electrical leads.

21. The structure as set forth in claim 20 wherein said first and second electrical leads have an impedance approximately equal to the impedance of said first and second electrodes, and the impedance of said first and second leads increases toward said respective first and second electrodes.

22. The structure as set forth in claim 20 wherein said first and second electrodes include resistive material.

23. The structure as set forth in claim 20 further comprising a layer of semi-conductive material mounted over said first and second electrodes.

24. The structure as set forth in claim 23 further including a coating of dielectric material covering said non-conductive layer surrounding said first and second electrodes and said semi-conductive material.

25. The structure as forth in claim 20 wherein the ice detection system is mounted in, and substantially fills, a recess in the external surface of the structure.

* * * * *